US006833720B1

(12) United States Patent
Daubenspeck et al.

(10) Patent No.: US 6,833,720 B1
(45) Date of Patent: Dec. 21, 2004

(54) ELECTRICAL DETECTION OF DICING DAMAGE

(75) Inventors: Timothy H. Daubenspeck, Colchester, VT (US); Jeffrey P. Gambino, Westford, VT (US); Thomas L. McDevitt, Underhill, VT (US); Anthony K. Stamper, Williston, VT (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 10/604,572

(22) Filed: Jul. 31, 2003

(51) Int. Cl.⁷ .............................................. G01R 31/02
(52) U.S. Cl. ...................................... 324/763; 324/765
(58) Field of Search ................................. 324/763, 765

(56) References Cited

U.S. PATENT DOCUMENTS

| | | | |
|---|---|---|---|
| 4,775,831 A | 10/1988 | Annamalai | |
| 5,606,264 A | 2/1997 | Licari et al. | |
| 5,847,574 A | 12/1998 | Berry, Jr. et al. | |

FOREIGN PATENT DOCUMENTS

| | | |
|---|---|---|
| JP | 55-50170 | 4/1980 |
| JP | 58-221176 | 12/1983 |
| JP | 63-175778 | 7/1988 |
| JP | 63-191075 | 8/1988 |
| JP | 64-83166 | 3/1989 |
| JP | 2-269982 | 11/1990 |
| JP | 6-51017 | 2/1994 |

OTHER PUBLICATIONS

J. Lumsden et al., "An AC Impedance In Situ Methodology for Assessing High Reliability Performance of Plastic Encapsulated Microelectronics in Harsh Environments," May 2002, Electronic Components and Technology Conference, pp. 219–224.*

* cited by examiner

*Primary Examiner*—Evan Pert
(74) *Attorney, Agent, or Firm*—Scully, Scott, Murphy & Presser; William D. Sabo, Esq.

(57) ABSTRACT

Electrical detection is provided for dicing damage to moisture barrier/edge seals of IC chips which include a low-K dielectric material, a moisture barrier/edge seal for the IC chip, and a moisture damage sensor circuit positioned on the IC chip in proximity to the moisture barrier/edge seal. One or a plurality of moisture barrier/edge seals can be positioned along peripheral edges of the IC chip, and one or more moisture damage sensor circuit(s) can be positioned between the plurality of moisture barrier/edge seal(s), or between an active area of the IC chip and the moisture barrier/edge seal(s), or on a peripheral area of the IC chip outside of the moisture barrier/edge seal(s). The sensor circuit can comprises a single or a plurality of, via chain(s) including a plurality of vias connected in series, or wire monitor circuit(s) extending in a serpentine conductive path through a plurality of wiring levels and vias, or interconnect (s), and the system can monitor the resistance(s) or leakage (s) or ratio(s) of parameters of the sensor circuit(s).

20 Claims, 2 Drawing Sheets

ELECTRICAL DETECTION OF DICING DAMAGE

BACKGROUND OF INVENTION

1. Field of the Invention

The present invention relates generally to electrical detection of dicing damage to IC (integrated circuit) chips. More particularly, the subject invention pertains to a method and system for electrical detection of damaged moisture barrier/edge seals on IC chips which include a low-K dielectric material, a moisture barrier/edge seal for the IC chip, and a moisture damage sensor circuit positioned on the IC chip in proximity to the moisture barrier/edge seal.

One or a plurality of moisture barrier/edge seals can be positioned along peripheral edges of the IC chip, and one or more moisture damage sensor circuit(s) can be positioned between the plurality of moisture barrier/edge seal(s), or between an active area of the IC chip and the moisture barrier/edge seal(s), or on a peripheral area of the IC chip outside of the moisture barrier/edge seal(s). The sensor circuit is comprised of a single or a plurality of, via chain(s) including a plurality of vias connected in series, or wire monitor circuit(s) extending in a serpentine conductive path through a plurality of wiring levels and vias, or interconnect (s), and the system can monitor the resistance(s) or leakage(s) or ratio(s) of parameters of the sensor circuit(s).

2. Discussion of the Prior Art

During an IC chip dicing operation, cracks can propagate into the active area of the IC chip, causing fails. Inspections are generally performed after dicing to make sure cracks have not propagated into the chip. Performing an optical microscope inspection on the edges of samples of a chip population is satisfactory for IC chips with conventional SiO2 dielectrics which do not rely on an edge seal.

However, for IC chips with low K dielectrics and moisture barrier/edge seals, this microscopic optical inspection approach can lead to reliability problems because it is expensive to inspect all IC chips, and also such microscopic optical inspections are somewhat subjective in nature.

IC chips with low K dielectrics and metal interconnects which do not form a self-passivating oxide layer, such as copper or silver interconnects, are susceptible to moisture ingress-induced corrosion, and accordingly moisture barrier/edge seals are required to prevent moisture from entering the IC devices. Water can diffuse through low K materials, such as polymers or porous glass, and oxidize the metal wires, causing their resistance to increase or causing leakage between wires due to a volume expansion associated with oxidation of the metal wires. If the moisture barrier/edge seal is damaged, then moisture can enter the IC device during operation, causing failure. Unfortunately, the failure can occur slowly, creating a reliability problem which is difficult to screen for. Therefore, it would be desirable to be able to detect IC chips with damaged moisture barrier/edge seals before they are shipped to customers.

SUMMARY OF INVENTION

Accordingly, it is a primary object of the present invention to provide for electrical detection of dicing damage to moisture barrier/edge seals of IC chips. The subject invention provides a system and method for detecting moisture penetration into an IC chip having an insulator which includes a low-K dielectric material, a moisture barrier/edge seal for the IC chip, and a moisture damage sensor circuit positioned on the IC chip in proximity to the moisture barrier/edge seal.

In greater detail, a plurality of moisture barrier/edge seals can be positioned along peripheral edges of the IC chip, and the moisture damage sensor circuit can be positioned between the plurality of moisture barrier/edge seals, or positioned between an active area of the IC chip and the plurality of moisture barrier/edge seals, or positioned on a peripheral area of the IC chip outside of the plurality of moisture barrier/edge seals.

A reference sensor circuit can also be positioned on the IC chip, and an electrical parameter such as the resistance or leakage or a ratio of the moisture damage sensor circuit compared to the same electrical parameter of the reference sensor circuit.

The sensor circuit can-comprise a via chain including a plurality of vias connected in series, or a wire monitor circuit extending in a serpentine conductive path through a plurality of wiring levels and vias of the IC chip.

A plurality of sensor circuits can be positioned along peripheral edges of the IC chip to detect when the moisture barrier/edge seal on the IC chip is damaged, and the plurality of sensor circuits can be wired together in series to form a single detection circuit. The plurality of sensor circuits can comprise a plurality of via chains or wiring levels or interconnects, and the system can monitor the resistances, or leakages, or ratios of the plurality of sensor circuits or of two neighboring sensor circuits.

BRIEF DESCRIPTION OF DRAWINGS

The foregoing objects of the present invention for electrical detection of dicing damage to IC chips may be more readily understood by one skilled in the art with reference being had to the following detailed description of several embodiments thereof, taken in conjunction with the accompanying drawings wherein like elements are designated by identical reference numerals throughout the several views, and in which.

DETAILED DESCRIPTION

Figure 1:
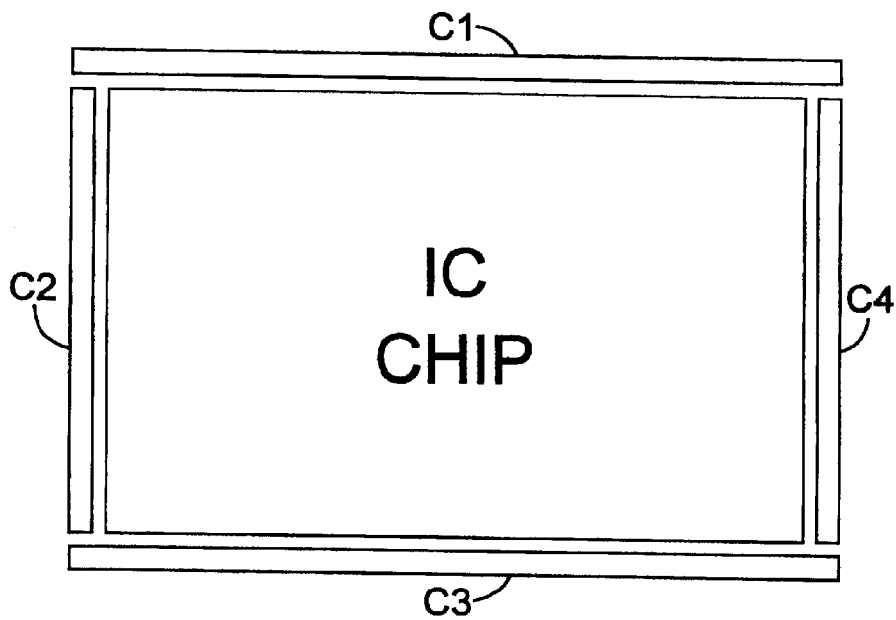
FIG. 1 illustrates the use of simple detection or sensor circuits on the edge of an IC chip to detect when a moisture barrier/edge seal on the IC chip is damaged.

FIG. 1 illustrates the use of simple detection or sensor circuits on the edge of an IC chip to detect when a moisture barrier/edge seal on the IC chip is damaged, and illustrates an IC chip having four detection circuits or sensors C1, C2, C3 and C4 positioned along the four length and width segments of the IC chip to surround the outer moisture barrier/edge seal of the IC chip. In one preferred embodiment, the four detection circuits or sensors C1, C2, C3 and C4 are four via chains as described in further detail below which are wired together in series to form a single detection or sensor circuit.

Some of the detection circuits that can be used for the sensors Cn are as follows:
- a via chain to monitor resistance of the via chain or resistance ratios of several via chains;
- an interconnect to monitor resistance of the interconnect or resistance ratios of several interconnects; and
- two neighboring interconnects to monitor leakage of the two neighboring interconnects or leakage ratios of the two neighboring interconnects.

Figure 2A:
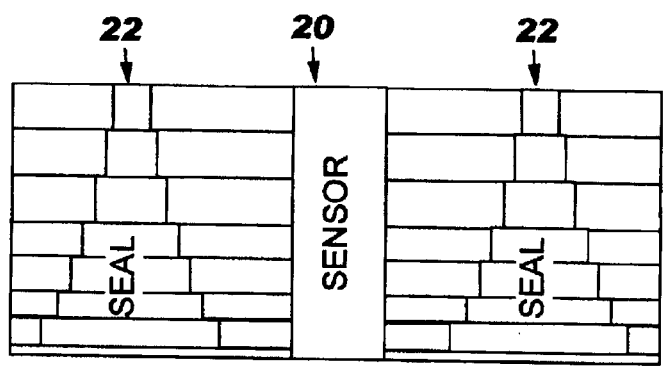
FIGS. 2(a) and 2(b) are cross sectional views of an integrated circuit chip having two moisture barrier/edge seals and a corrosion detector or sensor, with FIG. 2(a) showing the corrosion detector or sensor placed between the two moisture barrier/edge seals, and FIG. 2(b) showing the corrosion detector or sensor placed at the IC chip on the right side of the two moisture barrier/edge seals.
Figure 2B:
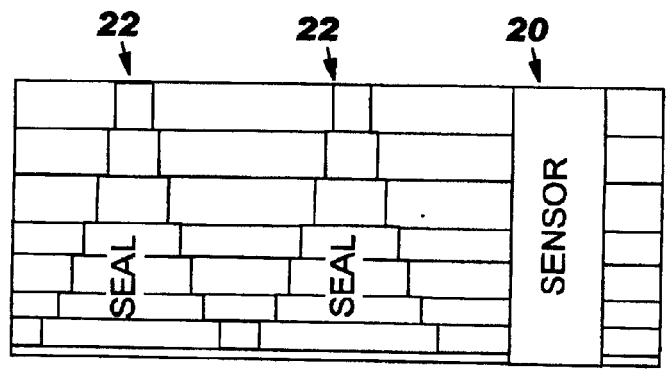

FIGS. 2(a) and 2(b) are cross sectional views of an integrated circuit chip having two moisture barrier/edge seals and a corrosion detector or sensor, with FIG. 2(a) showing the corrosion detector or sensor 20 placed between the two moisture barrier/edge seals 22, and FIG. 2(b) showing the corrosion detector or sensor 20 placed at the IC chip on the right side of the two moisture barrier/edge seals 22.

FIG. 2(b) actually represents two different embodiments, a first embodiment wherein the active circuit area of the IC chip is to the left of the two moisture barrier/ edge seals such that the corrosion detector or sensor is placed on the IC chip peripheral area outside of the two moisture barrier/edge seals, and a second embodiment wherein the active circuit area of the IC chip is to the right of the corrosion detector or sensor such that the corrosion detector or sensor is placed on the IC chip inside of the two moisture barrier/edge seals. Accordingly, FIG. 2 illustrates the placement of the corrosion detector or sensor circuit adjacent to two moisture barrier/edge seals on an IC chip, either outside the moisture barrier/edge seals or inside the moisture barrier/edge seals. If the corrosion detector or sensor circuit is placed outside the moisture barrier/edge seal, it will be affected by any dicing defect that affects the moisture barrier/edge seal. If the corrosion detection or sensor circuit is placed inside the moisture barrier/edge seal, it will be affected after the outer moisture barrier/edge seal is damaged during dicing.

The detector or sensor circuit could be used during a burn-in process at high temperatures and humidities to detect moisture barrier/edge seal fails, before the diced and/or packaged IC chip is shipped. In either case, whether the detector or sensor circuit is placed outside the moisture barrier/edge seal(s) or is placed inside the moisture barrier/edge seal(s), dicing damage that extends to the moisture barrier/edge seal(s) will cause the resistance of the detector or sensor circuit to increase. By sensing this resistance of the detector or sensor circuit as part of the built-in self-test of the chip, it is possible to determine if the moisture barrier/edge seal(s) has been damaged or not.

To improve sensitivity, the resistance (or leakage) of the damage detector or sensor device can be compared to a reference device; if the damage detector or sensor is broken up into multiple sections (e.g. one sensor per side of the IC chip), then the resistance ratios of the multiple sections can be used to determine if one sensor section has been damaged.

The use of control sensor structures with identical designs is preferred but is not required, since wire resistance and via resistance or wire to wire leakage current shifts slightly during a normal 10 year period of operation of an IC chip, and normalizing each control sensor structure to a reference control sensor structure eliminates these shifts in operating parameters. If a change or shift in a resistance or leakage current is detected, the IC part is flagged or scrapped. This method can be used to screen IC parts that have poor reliability due to damaged moisture barrier/edge seals.

Control detector or sensor structures can also be placed inside the IC chip to sense non-edge seal related fails. Exemplary applications would place these control detector or sensor structures around fuse bays and/or around C4/wirebond pads.

Figure 3:
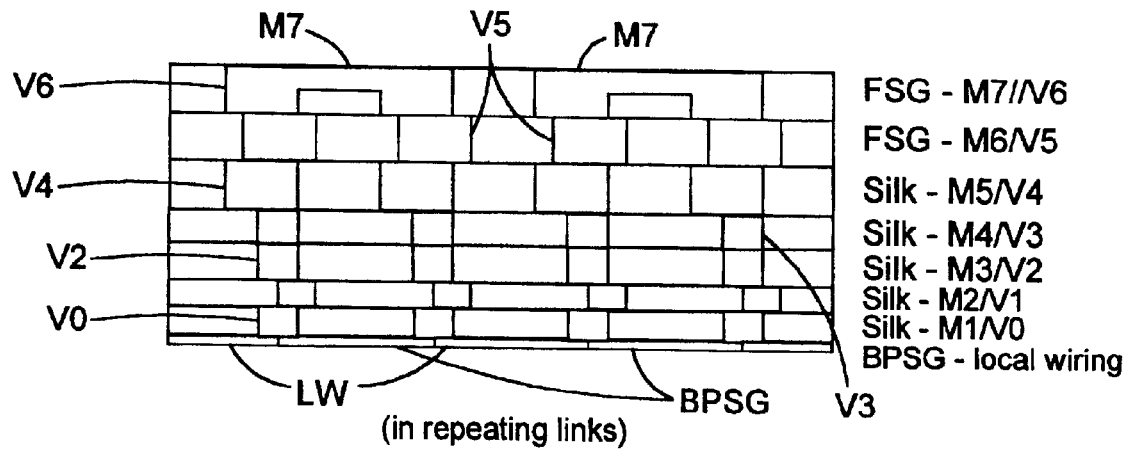
FIG. 3 is a cross sectional view of a preferred embodiment of a stacked via chain detector or sensor circuit for a 7 level of metal integrated circuit.
Figure 4:
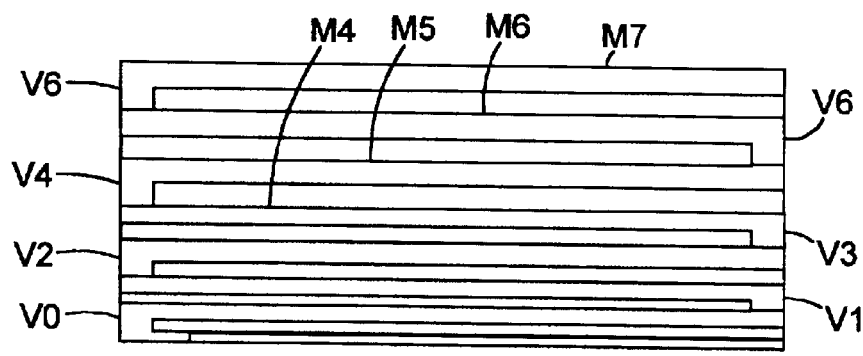
FIG. 4 is a cross sectional view of a single level wire sensor circuit which extends over a plurality of wire levels connected in series by vias at opposite ends of each wiring level, such that the conductive wire path of the sensor circuit forms a serpentine conductive path which zig zags back and forth over wire levels and vias of the IC chip.
Figure 5:
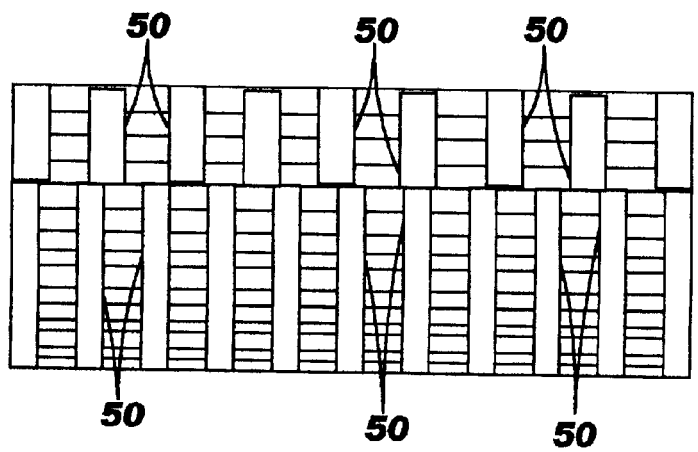
FIG. 5 is a cross sectional view of a stacked wire monitor which combines the approaches of the embodiments of FIGS. 3 and 4.

In each of the embodiments of FIGS. 3–5, an exemplary integrated circuit includes a lowest layer comprised of BPSG (borophoso silicate glass) separating metal conductive local wiring segments LW, and having seven metal layers M1–M7 on top thereof. The metal layers are designated M1–M7 and have vias designated V0–V6 therein. As an example, and illustrated on the right, metal layers M1–M5 might have a low K dielectric such as Silk, which is a trade name of Dow Corning for a polymer low K dielectric, and metal layers M6–M7 might have a low K dielectric of FSG (fluoro silicate glass).

FIG. 3 is a cross sectional view of a preferred embodiment of a stacked via chain detector or sensor circuit for a 7 level of metal integrated circuit. The stacked via chain is a preferred embodiment as it is a very sensitive structure to water ingress into an IC part. The vias V0–V6 are shown staggered which represents slight misalignments of the masks used to form the vias, and the via chain connection starts at the bottom local wiring segment LW and proceeds upwardly through successive vias V0–V6, and crosses over through a top metal connector M7, and then proceeds downwardly through successive vias V6–V0 to the next local wiring segment 32, and etc. to form a serpentine conductive path.

FIG. 3 illustrates a via-chain monitor for a via chain starting at PC, diffusion, or MC level and ending at last metal. For example, for a 6 level of metal PowerPC chip. the via chain would loop up and down using MCCA M1–V1–M2–V2–M3–V3–M4–VC–MG–VC–MG–VC–M4–V3 M3–V2–M2–V1–M1–CA–MC–CA–. . . .

This via chain would be placed to surround the entire IC chip, and preferably is broken up into two or more separate via chains, similar to the embodiment of FIG. 1 which has four via chains (C1, C2, C3, C4). The resistance ratio of each via chain to one or more control via chains, inside the IC chip, or to each other would be measured prior to the burn-in process. After burn-in, or at anytime in the future, including when the IC chip is in the field, if the resistance ratio shifts above a predetermined threshold, then the IC chip would be flagged as having a corrosion fail.

The magnitude of the resistance for the via-chain monitor in FIG. 3 is estimated for a 10 mm*10 mm chip, assuming the following:
- 4 ohms per via chain or stack,
- 0.5 ohms/square MC or silicide sheet resistance,
- 0.05 ohms/square copper wire sheet resistance,
- 3 micron on center spacing between adjacent via chains or stacks,
- 150 nm MC or silicide width,
- 1-micron last metal copper wire width.

Using these values results in the following calculated resistance for an undamaged test structure:.

Total via contact resistance=4*10000 microns*4 ohms/3 microns=53.3-kOhm.

Total MC or silicide resistance=0.5 ohms*40000 microns/ 0.2 microns=100-kOhm.

Total last metal copper wire resistance=0.05 ohms* 40000 microns/1 micron=2-kOhm.

Total via chain monitor resistance=53.3 +100 +2 kOhm ~155-kOhm.

FIG. 4 is a cross sectional view of a single level wire sensor for a 7 level of metal integrated circuit wherein the compositions of the individual layers of the embodiment of FIG. 4 could be the same as described with respect to the embodiment of FIG. 3. The sensor circuit comprises a plurality of wire levels M1-M7, with a minimum of two vias Vn per wiring level, and the plurality of wire levels M1–M7 are connected in series by vias V0–V6 at opposite ends of each wiring level extending between the wiring levels, such that the conductive wire path of the sensor circuit forms a serpentine conductive path which zig zags back and forth over wire levels and vias of the IC chip. The wire sensor of FIG. 4 can be used to sense a corrosion fail in the same manner as the previously described via chain monitor.

FIG. 4 illustrates a wire monitor wherein the conductive wire path starts at the local wiring level LW on the bottom left, proceeds up through via V0 on the left, extends from left to right through wire M1, proceeds up through via V1 on the right, extends from right to left through wire M2, and etc. in a serpentine conductive path. In this embodiment, the length of wires is much longer than that in FIG. 3, but the number of vias is much less. Therefore, the wire monitor in FIG. 4 will be more sensitive to defects that mainly cause corrosion of wires, whereas the via monitor in FIG. 3 will be more sensitive to defects that mainly cause corrosion of vias. Another advantage of the wire monitor compared to the via monitor is that it will have considerably lower resistance.

The magnitude of the resistance for the wire monitor in FIG. 4 is estimated for a 10 mm*10 mm chip, assuming the following:

0.05 ohms/square copper wire resistance, 0.5-micron average wire width,

Using these values results in the following calculated resistance for an undamaged test structure Total wire resistance=7 levels*0.05 ohms*40000 microns/0.5 micron=28-kOhm.

FIG. 5 is a cross sectional view of a single level wire sensor for a 7 level of metal integrated circuit. The compositions of the individual layers of the embodiment of FIG. 5 could be the same as described with respect to the embodiment of FIG. 3. FIG. 5 illustrates a stacked wire monitor which combines the approaches of the embodiments of FIGS. 3 and 4, wherein wires are stacked up MC, M1, M2, . . . LM, and wind in a serpentine conductive path around the IC chip similar to the embodiment of FIG. 4, and in addition the structure includes a high density of additional internal vias 50 similar to the embodiment of FIG. 3. The stacked wire monitor of FIG. 5 is useful to lower the overall resistance of the detector or sensor circuit. The embodiment of FIG. 5 can be used to sense a corrosion fail in the same manner as the previously described via chain monitor.

The magnitude of the resistance for the stacked wire monitor in FIG. 5 is estimated for a 10 mm*10 mm chip, assuming the following:

0.05 ohms/square copper wire resistance, 0.5-micron average wire width,

Using these values results in the following calculated resistance for an undamaged test structure Single level wire resistance=0.05 ohms*40000 microns /0.5 micron=4-kOhm, 1/Total wire resistance=7*(1/single level wire resistance)=7/(4000) =1/571, Total wire resistance~600 ohms.

A further embodiment can use a wire-to-wire leakage sensor consisting of electrically isolated adjacent wires running parallel to each other, side by side and/or stacked above each one, If a crack propagated to the moisture barrier/edge seal, resulting in copper corrosion, copper nodule corrosion byproducts would increase the wire to wire leakage currents, which are sensed to determine a corrosion fail.

In further embodiments, a combination of these or other similar structures can be combined together into a sensor for optimal sensitivity to a single chip crack-induced edge seal corrosion occurrence.

While several embodiments and variations of the present invention for a electrical detection of dicing damage are described in detail herein, it should be apparent that the disclosure and teachings of the present invention will suggest many alternative designs to those skilled in the art.

What is claimed is:

1. A system for detecting moisture penetration into an integrated circuit (IC) chip comprising:

an IC chip having an insulator which includes a low-K dielectric material;

a moisture barrier/edge seal for the IC chip; and a moisture damage sensor circuit positioned on the IC chip in proximity to the moisture barrier/edge seal.

2. The system of claim 1, including a plurality of moisture barrier/edge seals positioned along peripheral edges of the IC chip, and the moisture damage sensor circuit is positioned between the plurality of moisture barrier/edge seals to detect when a moisture barrier/-edge seal on the IC chip is damaged.

3. The system of claim 1, including a plurality of moisture barrier/edge seals positioned along peripheral edges of the IC chip, and the moisture damage sensor circuit is positioned between an active area of the IC chip and the plurality of moisture barrier/edge seals to detect when a moisture barrier/edge seal on the IC chip is damaged.

4. The system of claim 1, including a plurality of moisture barrier/edge seals positioned along peripheral edges of the IC chip, and the moisture damage sensor circuit is positioned on a peripheral area of the IC chip outside of the plurality of moisture barrier/edge seals.

5. The system of claim 1, wherein the system further comprises a reference sensor circuit positioned on the IC chip, and the resistance of the moisture damage sensor circuit is compared to the resistance of the reference sensor circuit.

6. The system of claim 1, wherein the system further comprises a reference sensor circuit positioned on the IC chip, and the leakage of the moisture damage sensor circuit is compared to the leakage of the reference sensor circuit.

7. The system of claim 1, wherein the sensor circuit comprises a via chain including a plurality of vias connected in series to form the sensor circuit.

8. The system of claim 1, wherein the IC chip comprises a plurality of wiring levels, and the sensor circuit comprises a wire monitor circuit extending through a plurality of wiring levels, with a minimum of two vias per wiring level, and the plurality of wiring levels are connected in series by the vias extending between the wiring levels, such that the conductive wire path of the sensor circuit forms a serpentine conductive path which zig zags back and forth over the wiring levels and the vias of the IC chip.

9. The system of claim 8, wherein the sensor circuit comprises a stacked wire sensor circuit having additional vias connected between the plurality of wiring levels to lower the overall resistance of the stacked wire sensor circuit.

10. The system of claim 1, including a plurality of sensor circuits positioned along peripheral edges of the IC chip to detect when the moisture barrier/edge seal on the IC chip is damaged.

11. The system of claim 10, wherein the plurality of sensor circuits comprise a plurality of via chains.

12. The system of claim 10, wherein the plurality of sensor circuits comprises a plurality of interconnects.

13. The system of claim 10, wherein the system monitors the resistance ratios of the plurality of sensor circuits.

14. The system of claim 10, wherein the system monitors the leakage of two neighboring sensor circuits.

15. The system of claim 10, wherein the system monitors the leakage ratios of two neighboring sensor circuits.

16. The system of claim 10, wherein the plurality of sensor circuits are wired together in series to form a single detection circuit.

17. A method for detecting moisture penetration into a conductor on an integrated circuit (IC) chip comprising an insulator which includes a low-K dielectric material, comprising:

forming an edge seal for the IC chip; and placing a moisture sensor on the IC chip in proximity to the edge seal.

18. The method of claim 17, further comprising positioning a reference sensor circuit on the IC chip, and comparing an electrical parameter of the moisture damage sensor circuit to the same electrical parameter of the reference sensor circuit.

19. The method of claim 17, further comprising positioning a plurality of sensor circuits along peripheral edges of the IC chip to detect when the moisture barrier/edge seal on the IC chip is damaged.

20. The method of claim 19, further comprising wiring the plurality of sensor circuits together in series to form a single detection circuit.

* * * * *